(12) United States Patent
Nordén et al.

(10) Patent No.: US 7,338,667 B2
(45) Date of Patent: Mar. 4, 2008

(54) PHARMACEUTICAL FORMULATION

(75) Inventors: Inger Nordén, Höör (SE); Catarina Carling, Malmö (SE); Peter Fyhr, Bjärred (SE)

(73) Assignee: Watson Pharmaceuticals, Inc., Corona, CA (US)

( * ) Notice: Subject to any disclaimer, the term of this patent is extended or adjusted under 35 U.S.C. 154(b) by 38 days.

(21) Appl. No.: 10/342,222

(22) Filed: Jan. 15, 2003

(65) Prior Publication Data

US 2003/0108606 A1 Jun. 12, 2003

Related U.S. Application Data

(63) Continuation of application No. 09/788,414, filed on Feb. 21, 2001, now abandoned.

(51) Int. Cl.
*A61K 9/20* (2006.01)
*A61K 9/14* (2006.01)

(52) U.S. Cl. ............... 424/464; 424/465; 424/468; 424/484; 424/488; 514/777; 514/781; 514/960; 514/369; 514/355; 514/563

(58) Field of Classification Search ............... 424/489, 424/490, 464, 465, 468, 484, 488, 493, 494, 424/495; 514/777, 781, 960, 961, 964
See application file for complete search history.

(56) References Cited

U.S. PATENT DOCUMENTS

| 4,803,081 | A | * | 2/1989 | Falk et al. ............... 424/488 |
| 5,451,409 | A | | 9/1995 | Rencher et al. |
| 5,593,695 | A | * | 1/1997 | Merrill et al. ............... 424/480 |
| 6,132,772 | A | * | 10/2000 | Sherman ............... 424/489 |
| 6,555,139 | B2 | * | 4/2003 | Sharma ............... 424/489 |

FOREIGN PATENT DOCUMENTS

| EP | 0 776 660 A2 | 6/1997 |
| EP | 0 852 141 A1 | 7/1998 |
| WO | WO 99/01121 A1 | 1/1999 |

OTHER PUBLICATIONS

International-Type Search Report dated Sep. 28, 2001 issued in the parent application's (U.S. Appl. No. 09/788,414) Swedish counterpart (i.e., No. 0004671-4).

* cited by examiner

*Primary Examiner*—Johann R. Richter
*Assistant Examiner*—Konata M. George
(74) *Attorney, Agent, or Firm*—Thorpe North & Western LLP

(57) ABSTRACT

The present invention concerns an extended release formulation having an accelerating erosion and/or dissolution rate of the surface of the formulation. The formulation comprises a drug having low solubility in water dispersed or dissolved in at least one erasable hydrophilic polymeric matrix.

9 Claims, 4 Drawing Sheets

PHARMACEUTICAL FORMULATION

This application is a continuation divisional of application User. No. 09/788,414, filed on Feb. 21, 2001 now abandoned.

FIELD OF THE INVENTION

The present invention is related to controlled release preparations. Especially the invention is related to controlled release pharmaceutical preparations including active compounds having low solubility in water and to methods of preparing such preparations.

BACKGROUND OF THE INVENTION

It is known to obtain sustained release of an active substance, e.g. Ea pharmaceutically active powder, by embedding it in a matrix of an insoluble substance from which the active substance will gradually diffuse.

Sustained release of an active substance contained in a tablet core may also be achieved by applying to the core a semipermeable coating through which water and dissolved active substance may diffuse or an insoluble coating provided with a hole through which the active substance is released.

Gradual release of an active substance may furthermore be obtained by micro encapsulating particles of an active substance in one or more layers of film which may be of different types, e.g. Of a type which mediates diffusion of the active substance or release thereof in the intestines.

The dissolution of materials dMF/dTA in a solvent is described by the Noyes Whitney equation:

$$\frac{dM}{dt} = \frac{AD(Cs - C)}{h}$$

where A is the area subjected to the solvent, D the diffusion coefficient, CSW the saturation concentration, C the concentration in the bulk solution and h the thickness of the diffusion gradient. Given that convective mixing is fairly constant and that sink condition is maintained, all parameters are constant except the area that is decreasing due to the dissolution. Consequently the release rate as a function of time will depend on the geometry of the dissolving species. The dissolution of a powder is well described by the Hiss-Cromwell Cube-Root Law (Martin A. Physical Pharmacy 4:th ed. Philadelphia: Lea & Febiger; 1993).

Other types of known pharmaceutical formulations having extended release are based on eroding hydrophilic matrices and the present invention concerns this type of formulations. In these formulations the release may be described by $$M(t)/M(\infty) = k \cdot t^n$$

where n reflects the basic kinetics of the release (Ritger and Peppas, J. Control. Real. 5(1987)23-26). The most beneficial situation is when the release rate is independent of the fraction of substance remaining in the formulation, changes in diffusion path length or the geometry of the system (i.e. n=1).

The Hopfenberg function gives a general function describing the dissolution of different shaped objects:

$$\frac{M_t}{M_\infty} = 1 - \left[1 - \frac{kt}{C_0 r_0}\right]^n$$

where $M_t$ and $M_\infty$ in the above formulas are the amount released at time t and infinite time, $C_0$ is the drug concentration and $r_0$ is the initial radius of the dissolving material, n is 1 for a slab of constant radius, 2 for a rod of constant length and 3 for a sphere. Constant release rate from dissolving objects can only be achieved by maintaining constant dissolving area {Robinson JR, Lee VHL. Controlled Drug Delivery, New York; Marcel Dekker; 1987, 8650}). Such systems have been suggested by coating the rim of a tablet with a water impermeable coating {Colombo P, Conte U, Caramella C, Gazzaniga A, La Manna A. Compressed polymeric minimatrixes for drug release control. Journal of Controlled Release, 1985; 1(4) 240}). Another way is to compensate for the reducing area by increasing the drug concentration in the inner parts of the system {Robinson JR, Lee VHL. Controlled Drug Delivery, New York: Marcel Dekker; 1987, 520})

The release from an ordinary dissolving, eroding tablet is well described by $$\frac{M_t}{M_\infty} = 1 - \left(1 - \frac{k_r}{C_0 r_0} t\right)^2 \left(1 - \frac{2k_h}{C_0 h_0} t\right)$$

wherein $C_0$ is the concentration of drug in the matrix, $r_0$ and $h_0$ is the initial radius and height of the matrix, $k_r$ and $k_h$ are the erosion/dissolution rates of the radius and height respectively. This means that the rate of erosion/dissolution of the periphery may be different from that of the thickness due to different hydrodynamic conditions {Katzhendler, Hoffman, et al. 1997}

The dissolution of the excipients and the structure, e.g. porosity, of the matrix will largely control the release rate from a system containing a drug with low aqueous solubility. Contrary to previous and conventional eroding/dissolving systems the present invention provides a solution to the problem of constructing a eroding/disolving system wherein the the dissolution/erosion rate increases with time so that a constant release rate of the drug over extended periods of time is attained.

OBJECTS OF THE INVENTION

An object of the invention is to provide an extended release formulation that releases the pharmacologically active component at a constant rate independently of the decreasing area of the formulation over an extended period of time.

A second object of the invention is to provide an extended release formulation of a pharmacologically active substance having a low aqueous solubility.

A third object of the invention is to provide an extended release formulation that releases the active component by erosion and/or dissolution.

SUMMARY OF THE INVENTION

In brief the present invention concerns formulation having extended and essentially constant release rate. The new formulation is distinguished by an accelerating erosion and/or dissolution of the surface of the formulation. The formulation comprises a finely divided drug having low solubility in water dispersed or dissolved in at least one erasable hydrophilic polymeric matrix.

DETAILED DESCRIPTION OF THE INVENTION

Figure 1:
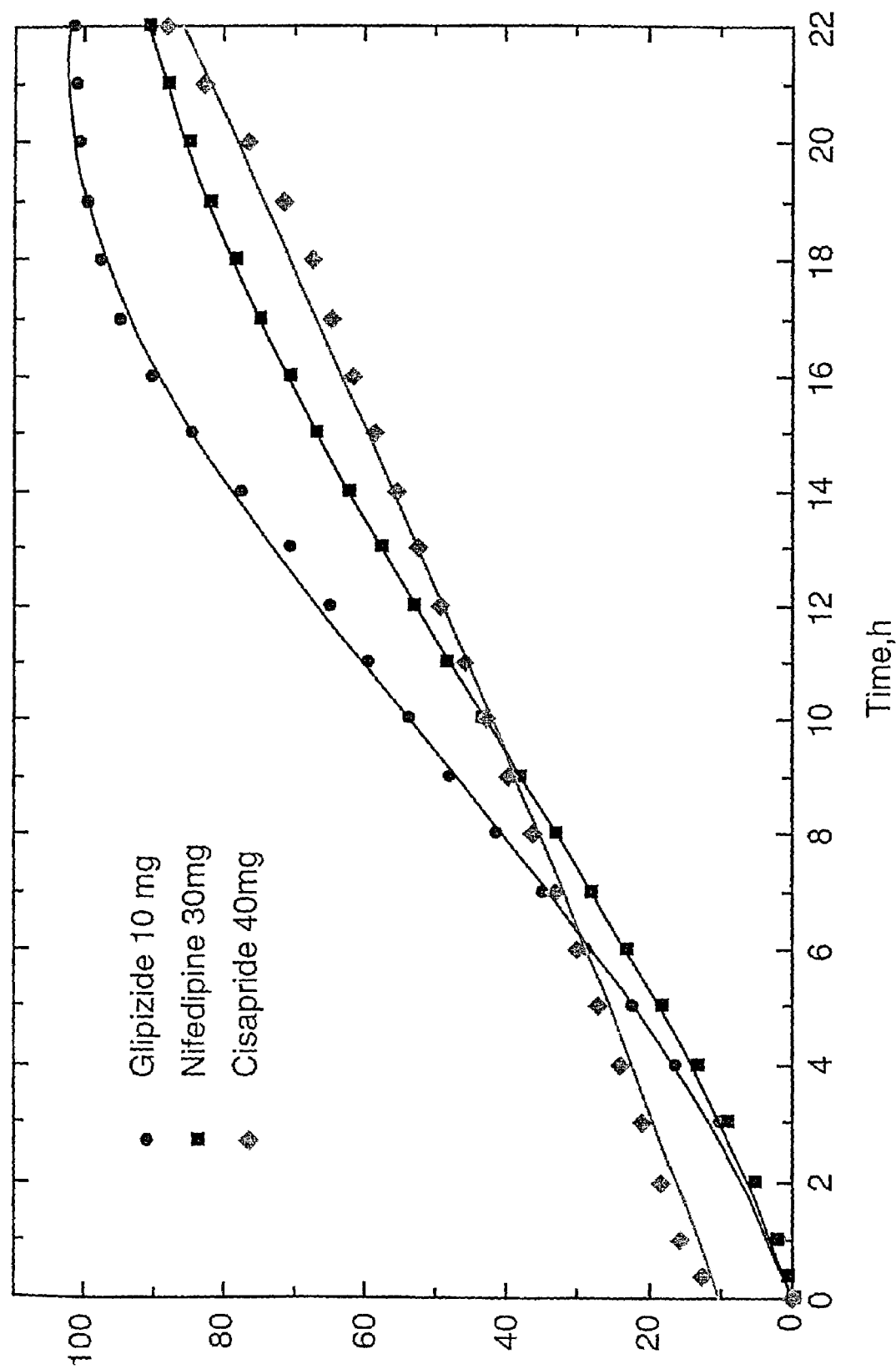
FIG. 1 shows comparative dissolution profile results of formulations containing 10 mg glipizide, 30 mg nifedipine, and 40 mg cisapride.

In order to obtain an essentially constant release rate according to the present invention the erosion/release rate must increase with time to compensate for the decreasing release surface area, which mathematically requires a modification where the release rate constants are functions of time.

$$\frac{Q_t}{Q_\infty} = 1 - \left(1 - \frac{(k_r + r_t t)}{C_0 r_0} t\right)^2 \left(1 - \frac{2(k_h + h_t t)}{C_0 h_0} t\right)$$

wherein $r_t$ and $h_t$ are the rate increase constants for radius and thickness.

In practice control of the release rate is thus performed by the following factors:
amount of active drug
type of matrix former
viscosity (i.e. degree of polymerisation, molecular weight) of the matrix former
amount of matrix former
type and amount of accelerating agent
type and amount of plasticiser
granulate size distribution
tablet geometry
compaction force Drug According to the present invention the drug is a pharmacologically active substance of low aqueous solubility which in this context means that the solubility should be less than 100 mg/ml. Particularly interesting drugs for which the invention is applicable are those having a solubility less than 20 mg/ml. Due to the low solubility of the drug the gradient driving diffusion of the drug through the hydrated polymer matrix is too small to allow for more than a minute fraction of the release rate.

Examples of drugs suitable for the release formulation according to the present invention are dicofenac sodium, glipizide, nifedipine, felodipine, cisapride maleate.

Matrix

The hydrophilic polymer matrix glues the particles, drug and excipients, together and acts to retard and control the dissolution of the matrix.

Examples of hydrophilic polymers forming the matrix are hydroxyethyl cellulose, hydroxypropyl cellulose, hydroxypropyl methylcellulose, guar gum, polyethylene oxide or a mixture thereof. The higher the proportion matrix former is the slower the release rate becomes and this is also used to control the release rate. Preferably the matrix former is a mixture of 1-10% by weight hydroxypropyl cellulose and 10-50% by weight hydroxyethyl cellulose, preferably 20-30%.

Osmotic/Accelerating Agent

This optional excipient is water soluble but otherwise inert material that is added in order to increase the thermodynamic water gradient into the tablet, thereby, accelerating the erosion/dissolution rate. Examples of such excipients are pharmaceutically acceptable water soluble substances eg. sugars such as lactose, sacharose, glucose, sugar alcohols such as sorbitol, mannitol, salts, such as sodium chloride. The accelerating agent should have a solubility of 300-1000 g/l, preferably 500-800 g/l and constitute 1-50% by weight, preferably 20-30% by weight of the formulation.

Plasticiser

Depending on the nature of the polymer, a plasticiser may be added in order to facilitate the deformation of granules during compaction. The plasticiser should be a GRAS (=Generally Regarded As Safe) non volatile agent capable of lowering the glass transition temperature of the matrix former. An example of a suitable plasticiser is low molecular weight polyethylene oxide which are in liquid form at room temperature (e.g. PEO 400).

Binder

A final optional excipient is a low viscosity polymer-binder. Examples of such binders are hydroxypropyl cellulose and polyvinyl pyrrolidone. One optional excipient may be inert filler to adjust the size of the matrix, particularly if the dose of the drug is low.

Lubricant

Any conventional lubricant such as magnesium stearate in amounts varying between 1 and 5% by weight may be used.

Granulation and Compaction

The components are wet granulated either using the matrix former as binder or by using an additional binder.

The release rate and the acceleration of the release rate is controlled by the rate of water transport into the matrix. This is apart from the composition also dependent on the porosity and structure of the matrix.

These factors are controlled by granulate size distribution, granulate plasticity, compaction force and pressure distribution. The latter highly dependent on the axial geometry of the compact.

To achieve appropriate function and reproducibility a free flowing granulate of narrow particle size distribution is essential. The granulate should be sufficiently plastic to deform under pressure and the axial geometry should be flat to achieve an even force distribution in the granulate bed.

The invention is further illustrated by the following examples:

EXAMPLE 1

Effect of different amounts matrix polymer

| Composition mg/tablet | |
|---|---|
| Glipizide | 10.0 |
| Hydroxyethyl cellulose (HEC) | 25.0 |
| (high viscosity quality | |
| Natrosol 250 M) | 6.0, 8.7, |
| | 12.0, 16.7, 20.0 |

-continued

| Composition mg/tablet | |
|---|---|
| Hydroxypropyl cellulose | 7.8 |
| Lactose | 55.2 |
| PEG 400 | 1.0 |
| Ethanol | 55.0 |
| Magnesium stearate | 1.0 |

Figure 4:
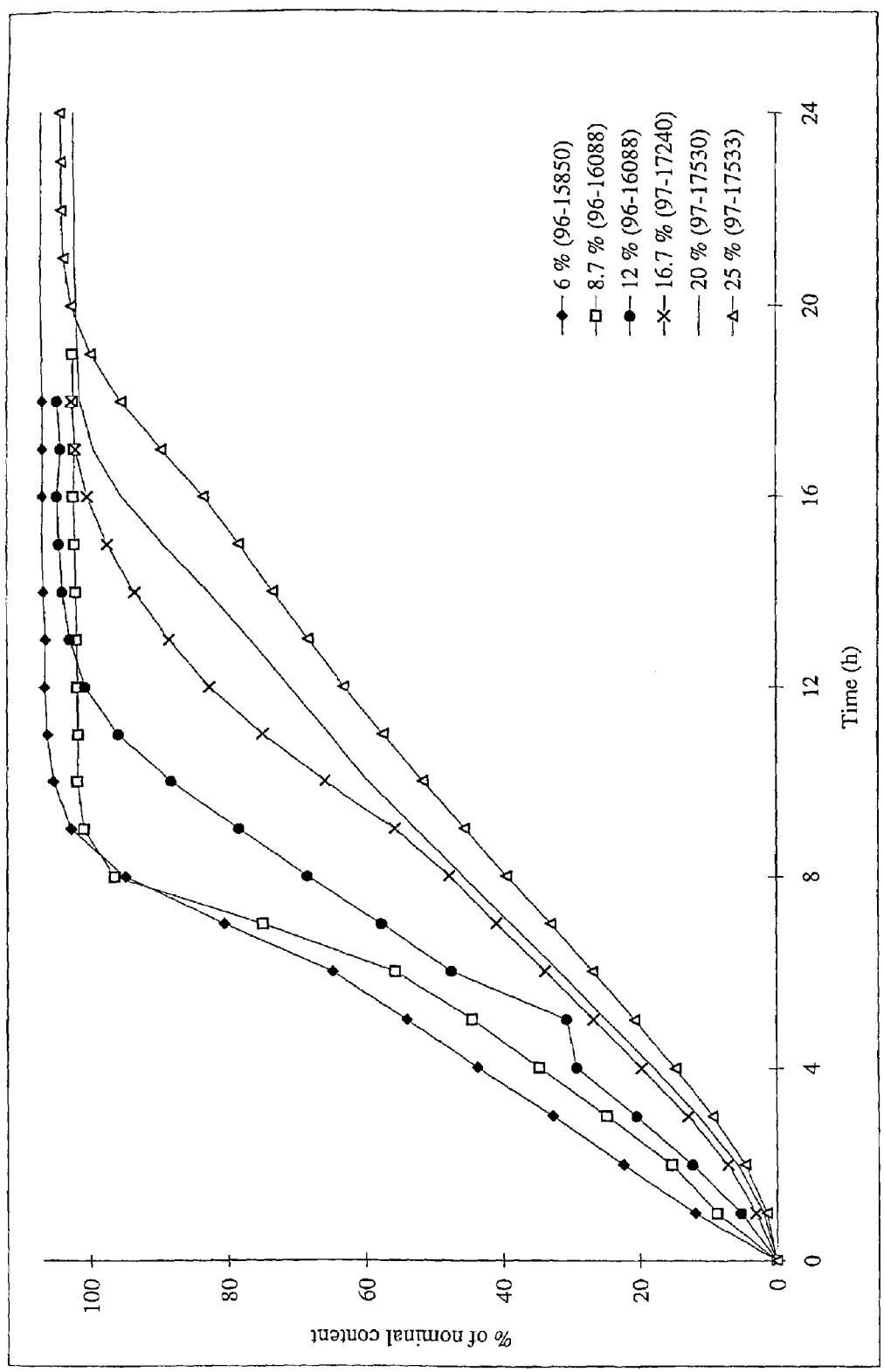
FIG. 4 shows comparative dissolution profile results of glipizide formulations utilizing differing amounts of hydroxyethylcellulose.

Glipizide, HEC, and lactose are sieved through a 1 mm sieve and dry mixed in an intensity mixer. HPC and PEG are dissolved in ethanol and stirred overnight to ensure complete swelling. The powder mixture is continuously granulated with the polymer solution in a fluidised bed. The dry granulate is finally mixed with magnesium stearate and the obtained mixture is compressed into a tablet having 6 mm diameter. Release profiles using the USP I method in 0.1 M phosphate buffer pH 6.8 are given in FIG. 4 which shows that the release rate can be controlled by the amount of HEC.

EXAMPLE 2

Effect of the matrix polymer viscosity and amount of polymeric matrix

| Composition mg/tablet | |
|---|---|
| Glipizide | 10.0 |
| Hydroxyethyl cellulose (high viscosity quality) or | 25.0 |
| Hydroxyethyl cellulose (low viscosity, Natrosol 250 HX) | 50.0 |
| Hydroxypropyl cellulose | 7.8 |
| Lactose | 55.2 |
| PEG 400 | 1.0 |
| Ethanol | 55.0 |
| Magnesium stearate | 1.0 |

Figure 3:
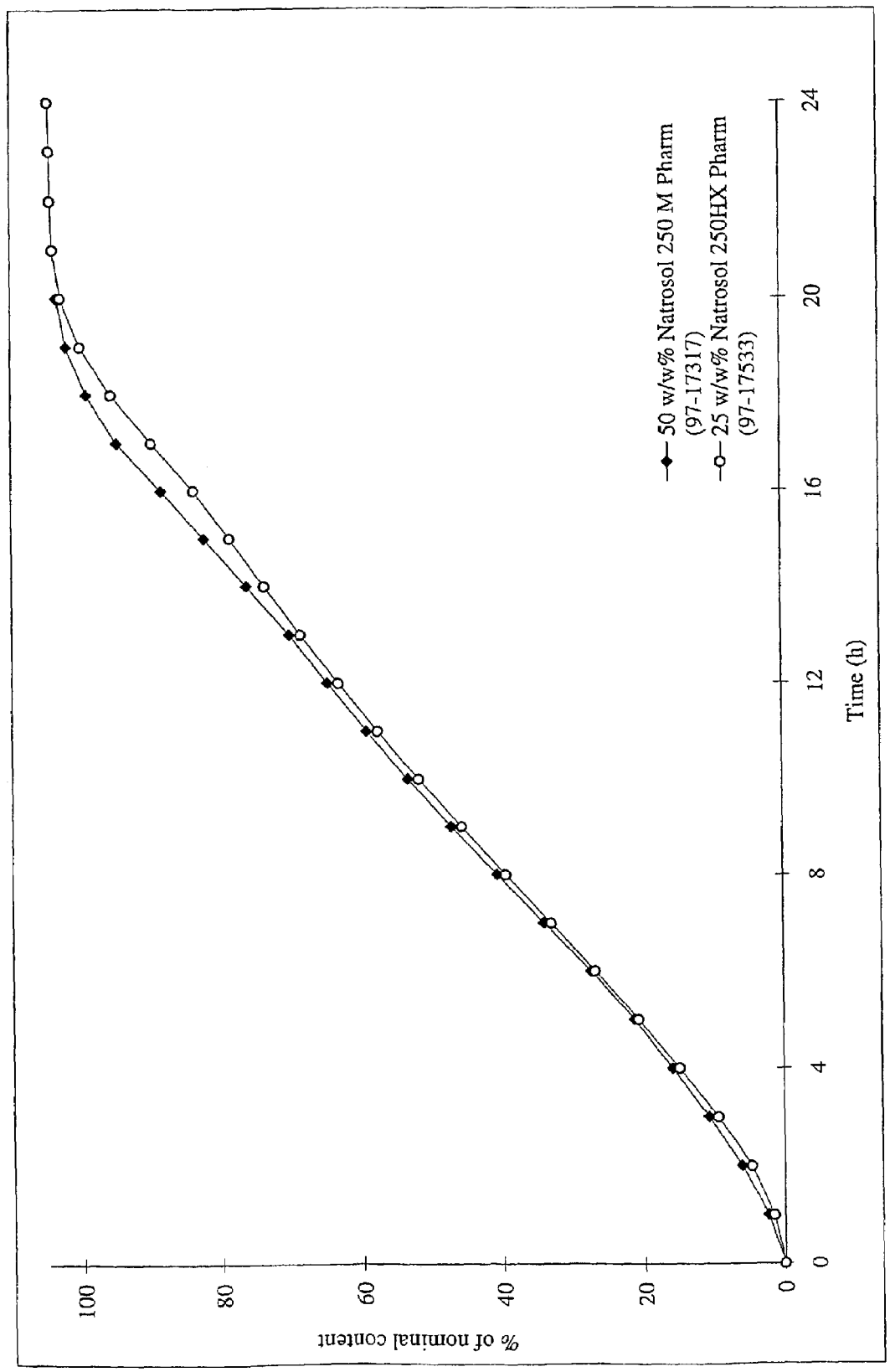
FIG. 3 shows comparative dissolution profile results of glipizide formulations utilizing hydroxyethylcellulose components of differing viscosity.

Manufacture and analysis are performed as in example 1. The release profile given in FIG. 3 shows that the low viscosity polymer requires twice the amount of the high viscosity polymer to obtain the same release rate.

EXAMPLE 3

Effect of amount of drug

| Composition mg/tablet | |
|---|---|
| Glipizide | 10.0 |
| Hydroxyethyl cellulose | 25.0 |
| Hydroxypropyl cellulose | 7.8 |
| Lactose | 55.2 |
| PEG 400 | 1.0 |
| Ethanol | 55.0 |
| Magnesium stearate | 1.0 |
| Glipizide | 5.0 |
| Hydroxyethyl cellulose | 5.0 |
| Hydroxypropyl cellulose | 7.8 |
| Lactose | 55.2 |
| PEG 400 | 1.0 |
| Ethanol | 55.0 |
| Magnesium stearate | 1.0 |

Figure 2:
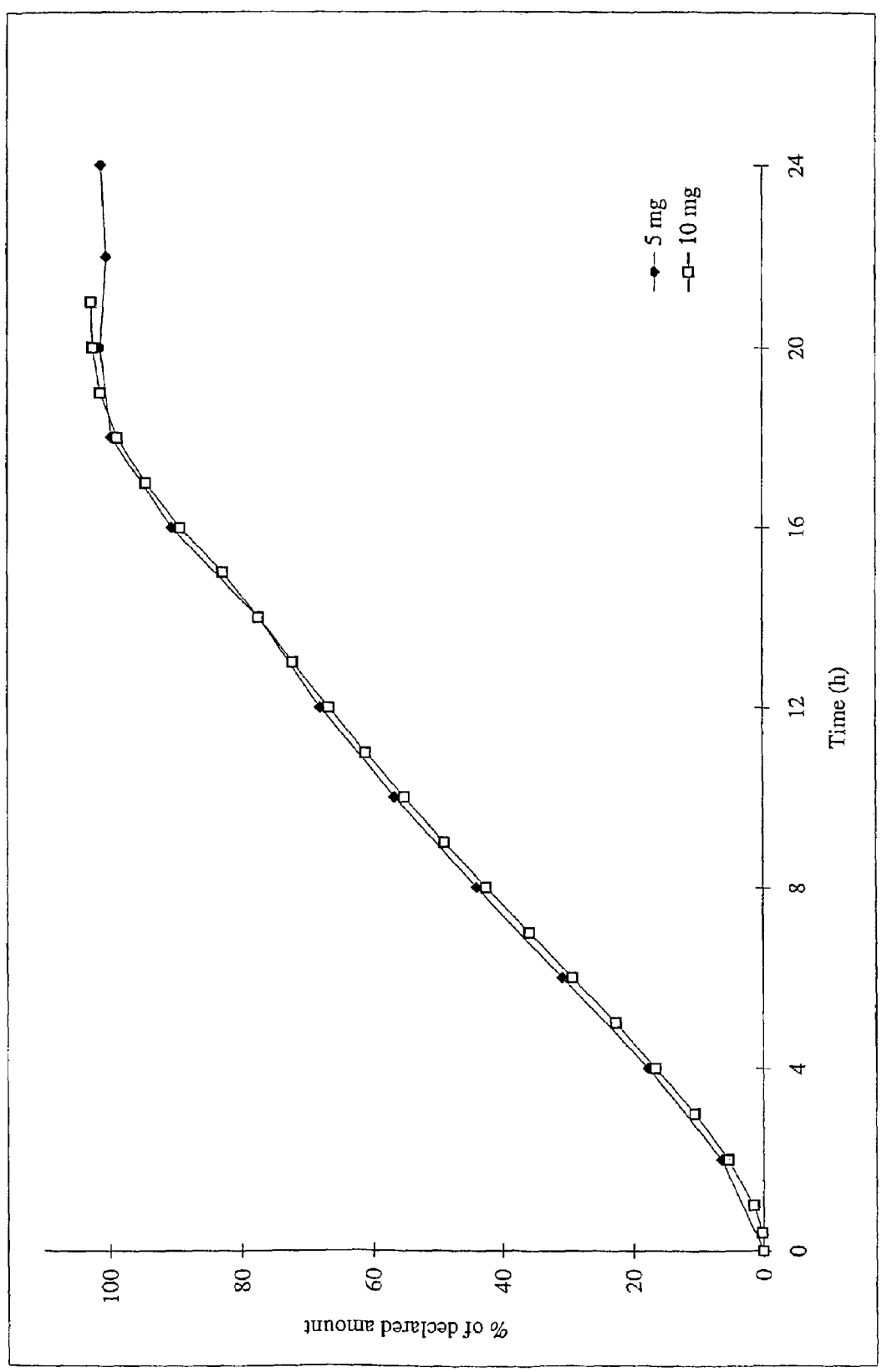
FIG. 2 shows comparative dissolution profile results of formulations containing 5 mg glipizide and 10 mg glipizide, respectively.

Manufacture and analysis are performed as in example 1. The release profile using the USP I method in 0.1 M phosphate buffer pH 6.8 as given in FIG. 2 shows that the release rate is controlled by the matrix and is less affected by the amount of drug.

EXAMPLE 4

| Composition mg/tablet | |
|---|---|
| Nifedipine | 30.0 |
| Hydroxyethyl cellulose | 25.0 |
| Hydroxypropyl cellulose | 7.8 |
| Lactose | 35.2 |
| PEG 400 | 1.0 |
| Ethanol | 55.0 |
| Magnesium stearate | 1.0 |

Manufacture is performed as in example 1. The release profile is given in FIG. 1.

EXAMPLE 5

| Composition mg/tablet | |
|---|---|
| Cisapride maleate | 40.0 |
| Hydroxyethyl cellulose | 25.0 |
| Hydroxypropyl cellulose | 7.8 |
| Lactose | 25.2 |
| PEG 400 | 1.0 |
| Ethanol | 55.0 |
| Magnesium stearate | 1.0 |

Manufacture is performed as in example 1. The release profile is given in FIG. 1.

The different release profiles obtained is probably explained by the different rates of dissolution of the drugs.

The invention claimed is:

1. An oral dosage formulation comprising:
   a drug selected from the group consisting of dicofenac sodium, glipizide, nifedipine, felodipine, and cisapride maleate; having low solubility in water dispersed or dissolved in at least one erodable hydrophilic polymeric matrix that includes a mixture of 1-10% by weight hydroxypropyl cellulose and 20-30% by weight high viscosity hydroxyethyl cellulose, wherein the matrix provides accelerated erosion in order to compensate for reduced surface area, and thereby maintain a controlled drug release; and
   an accelerating agent having a solubility of 300-1000 g/l.

2. The formulation according to claim 1, wherein the accelerating agent constitutes 1-50% by weight of the formulation.

3. The formulation according to claim 1, wherein the accelerating agent is a mono or di-saccharide.

4. The formulation according to claim 3, wherein the accelerating agent is selected from the group consisting of lactose, saccharose, glucose and fructose.

5. An oral dosage formulation comprising:
   a drug selected from the group consisting of dicofenac sodium, glipizide, nifedipine, felodipine, and cisapride maleate; having low solubility in water dispersed or dissolved in at least one erasable hydrophilic polymeric matrix that includes a mixture of 1-10% by weight hydroxypropyl cellulose and 20-30% by weight high viscosity hydroxyethyl cellulose, wherein the matrix provides accelerated erosion in order to compensate for reduced surface area, and thereby maintain a controlled drug release; and
   an accelerating agent having a solubility of 500-800 g/l.

6. The formulation according to claim 1, wherein the accelerating agent constitutes 20-30% by weight of the formulation.

7. The formulation according to claim 5, wherein the accelerating agent constitutes 1-50% by weight of the formulation.

8. The formulation according to claim 5, wherein the accelerating agent constitutes 20-30% by weight of the formulation.

9. The formulation according to claim 5, wherein the accelerating agent is a mono or di-saccharide.

* * * * *